(12) United States Patent
Struengmann et al.

(10) Patent No.: US 6,284,269 B1
(45) Date of Patent: Sep. 4, 2001

(54) PHARMACEUTICAL COMPOSITIONS OF MELOXICAM WITH IMPROVED SOLUBILITY AND BIOAVAILABILITY

(75) Inventors: Andreas Struengmann; Brigitte Freudensprung; Karin Klokkers, all of Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 09/486,463

(22) PCT Filed: Aug. 27, 1998

(86) PCT No.: PCT/EP98/05456

§ 371 Date: May 10, 2000

§ 102(e) Date: May 10, 2000

(87) PCT Pub. No.: WO99/09988

PCT Pub. Date: Mar. 4, 1999

(30) Foreign Application Priority Data

Aug. 27, 1997 (EP) .................................................. 97114816

(51) Int. Cl.$^7$ ...................................................... A61K 9/62
(52) U.S. Cl. ........................ 424/461; 424/462; 424/479; 424/493; 424/499
(58) Field of Search ................................... 424/468, 461, 424/493, 479, 462, 499

(56) References Cited

U.S. PATENT DOCUMENTS

| | | | | |
|---|---|---|---|---|
| 5,055,306 | * | 10/1991 | Barry et al. | 424/482 |
| 5,427,799 | * | 6/1995 | Valentine et al. | 424/451 |
| 5,840,881 | * | 11/1998 | Uda et al. | 536/46 |
| 5,965,163 | * | 10/1999 | Miller et al. | 424/468 |
| 6,068,855 | * | 5/2000 | Leslie et al. | 424/468 |
| 6,093,420 | * | 7/2000 | Baichwal | 424/468 |

OTHER PUBLICATIONS

Lakemedelsverket, Summary of Product Characteristics, Mobic, Nov. 1995.*

* cited by examiner

*Primary Examiner*—James H. Reamer
(74) *Attorney, Agent, or Firm*—Pitney, Hardin, Kipp & Szuch, LLP

(57) ABSTRACT

Pharmaceutical compositions containing enolic carboxamide type antiinflammatory agent meloxicam that exhibit improved wettability, aqueous solubility, dissolution behaviour over a broad range of pH, and that are prepared by crystal structure modification of the drug through dry or wet mechanical homogenization with two further components—one of them is selected from a group of oligo—and dissolution improving, or alkalizing agent. The application of the formulations according to the present invention results in an improved bioavailability and effectiveness of meloxicam.

22 Claims, 4 Drawing Sheets

Figure 1:
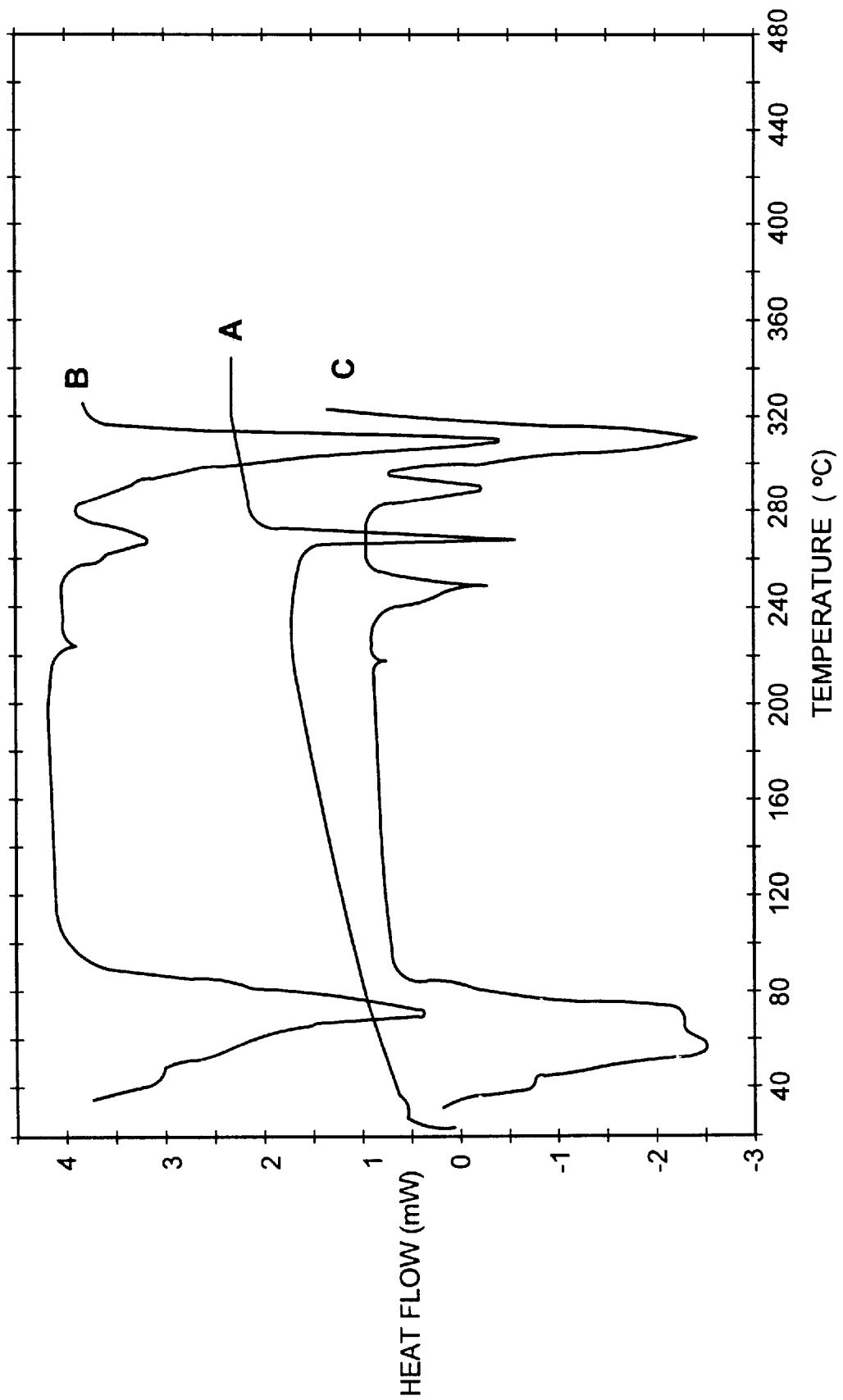

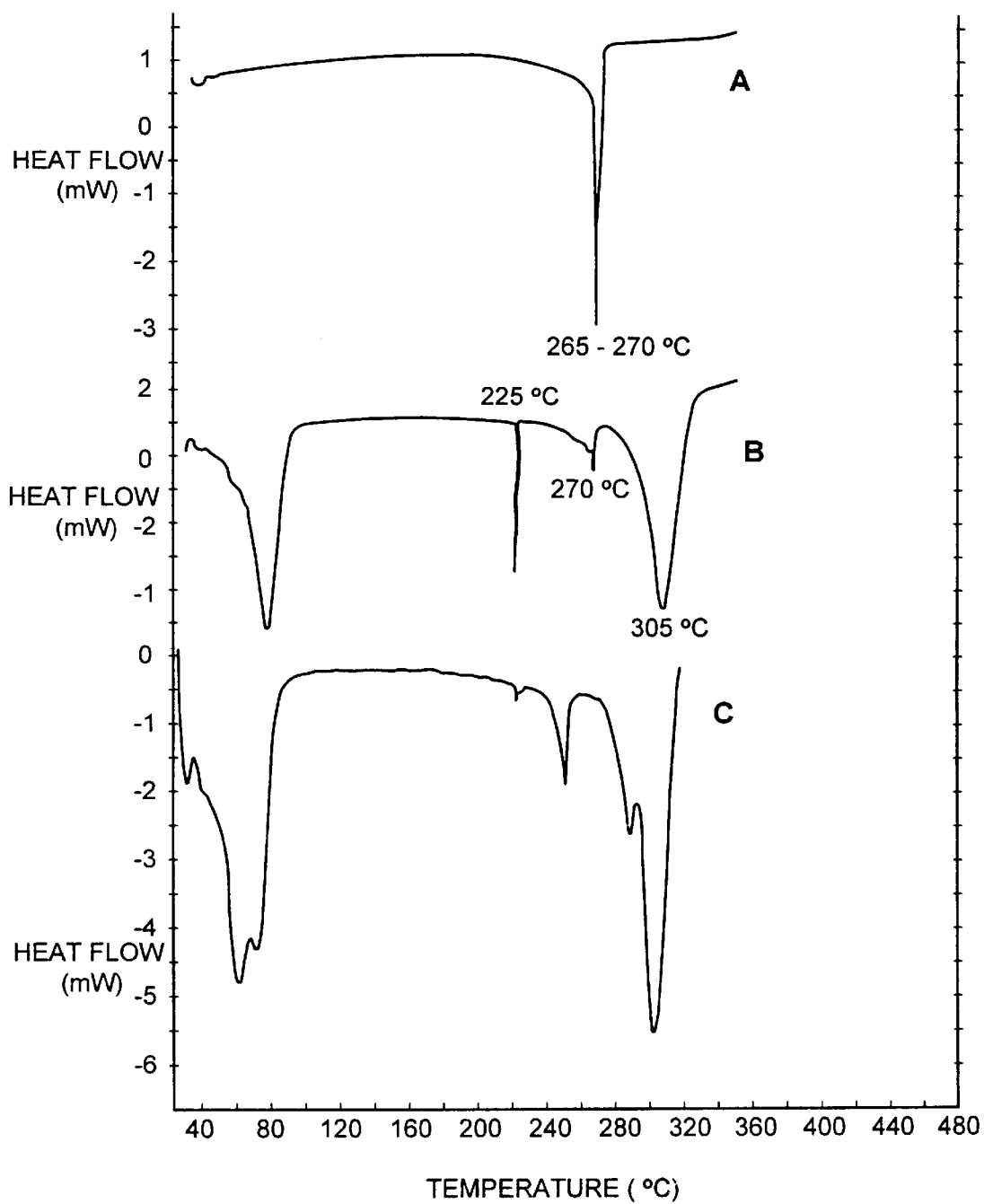
F I G. 2

PHARMACEUTICAL COMPOSITIONS OF MELOXICAM WITH IMPROVED SOLUBILITY AND BIOAVAILABILITY

PATENT CLAIMS

1. Pharmaceutical composition comprising meloxicam as active ingredient, a cyclodextrin, a facultative oligosaccharide other than cyclodextrin, a facultative polysaccharide, one or more pharmaceutically acceptable additives selected from the group consisting of
   surfactants,
   hydrotropic agents,
   alkalizing agents,
   hydrocolloids and
   polymers
and facultative excipients, carriers and/or auxiliary agents, wherein the pharmaceutical composition is obtainable by co-milling, co-grinding or co-kneading meloxicam in the presence of cyclodextrin as a pharmaceutically acceptable additive.

2. Composition according to claim 1, obtainable by micronizing meloxicam in the presence of a pharmaceutically acceptable additive.

3. Composition according to claim 1 or 2, obtainable by wet mechanical homogenization of its components in the presence of water, preferably in an amount of 5 to 50% by weight (based on the total weight of the composition).

4. Composition according to any of the preceding claims, characterized by microcrystalline cellulose and/or lactose and/or starch as oligo- or polysaccharide.

5. Composition according to any of the preceding claims, characterized by polyoxyethylene-sorbitan-mono-fatty acid, diethyleneglycol monoethylether and/or nonylphenol tetraethyleneglycol ether as surfactant.

6. Composition according to any of the preceding claims, characterized by an amount of 1 to 99 and preferably about 20% by weight of a hydrotropic agent (based on the total weight of the composition).

7. Composition according to any of the preceding claims, characterized by sodium glycinate, nicotinamide and/or methylglucamine as hydrotropic agent.

8. Composition according to any of the preceding claims, characterized by sodium carbonate, ammonium carbonate, sodium hydroxide, especially powdered sodium hydroxide, and/or sodium phosphate as alkalizing agent.

9. Composition according to any of the preceding claims, characterized by β-cyclodextrin hydrate (BCDx), 6-monoamino-beta-cyclodextrin (AMBCDx), gamma-cyclodextrin hydrate (GCDx), branched β-cyclodextrin, especially a branched β-cyclodextrin of the glycosyl/maltosyl substituted type or a β-cyclodextrin hydrate derivative, and/or hydroxypropyl-β-cyclodextrin as cyclodextrin, especially of a hydroxyalkylation degree in the range of 4.0 to 5.0.

10. Composition according to any of the preceding claims, characterized by methylcellulose-propylene-glycol ether, tris-hydroxymethylaminomethane, 2,6-diamino-hexanoic acid (D,L-lysine), mannitol, polyethyleneglycol, propyleneglycol, diethanolamine, ethyleneamine, monoethanolamine, triethanolamine, diisopropylamine, dibutylamine, pentylamine, sodium dodecylsulfate, methylglucamine, polyvinylpyrrolidone, cellulose ether, polyoxyethylene-polyoxypropylene-block-copolymers and/or nicotinamide as pharmaceutically acceptable additive.

11. Pharmaceutical composition comprising meloxicam as active ingredient, a cyclodextrin and a facultativen oligosaccharide or polysaccharide, water as aqueous vehicle, a co-solvent and facultative auxiliary agents, wherein the pharmaceutical composition is obtainable by micronizing meloxicam in the presence of the cyclodextrin, the facultative oligosaccharide or polysaccharide, water and a co-solvent as pharmaceutically acceptable additive.

12. Pharmaceutical composition comprising meloxicam as active ingredient, a cyclodextrin and a facultative oligosaccharide or polysaccharide, water as aqueous vehicle, a co-solvent and facultative auxiliary agents, obtainable by wet mechanical homogenization of its components in the presence of water, preferably in an amount of 5 to 50% by weight (based on the total weight of the composition).

13. Composition according to claim 11 or 12, characterized by β-cyclodextrin hydrate (BCDx), 6-monoamino-beta-cyclodextrin (AMBCDx), gamma-cyclodextrin hydrate (GCDx), branched β-cyclodextrin, especially a branched β-cyclodextrin of the glycosyl/maltosyl substituted type or a β-cyclodextrin hydrate derivative, and/or hydroxypropyl-β-cyclodextrin as cyclodextrin, especially of a hydroxyalkylation degree in the range of 4.0 to 5.0.

14. Composition according to any of claims 11 to 13, characterized by microcrystalline cellulose, lactose and/or starch as oligo- or polysaccharide.

15. Composition according to any of claims 11 to 14, characterized by an amount of 0.1 to 25 and preferably about 5.0% by weight co-solvent (based on the amount of water or on the total weight of the composition).

16. Composition according to any of claims 11 to 15, characterized by i-propanol, propyleneglycol, glycerol, polyethyleneglycol and/or ethanol as co-solvent.

17. Composition according to any of claims 11 to 16, characterized by one ore more additional pharmaceutical acceptable additives selected from the group consisting of surfactants, hydrotropic agents, alkalizing agents, hydrocolloids and polymers, preferably selected from the group consisting of methylcellulose-propylene-glycol ether, tris-hydroxymethylaminomethane, 2,6-diamino-hexanoic acid (D,L-lysine), mannitol, polyethyleneglycol, propyleneglycol, diethanolamine, ethyleneamine, monoethanolamine, triethanolamine, diisopropylamine, dibutylamine, pentylamine, sodium carbonate, sodium dodecylsulfate, ammonium carbonate, sodium hydroxide, especially powdered sodium hydroxide, sodium phosphate, methylglucamine, polyvinylpyrrolidone, cellulose ether, polyoxyethylene-polyoxypropylene-block-copolymers and/or nicotinamide as pharmaceutically acceptable additive.

18. Composition according to any of claims 11 to 17, characterized by an amount of 1 to 99 and preferably about 20% by weight of a hydrotropic agent (based on the total weight of the composition).

19. Composition according to any of the preceding claims for oral, rectal, transdermal, ophthalmic or parenteral administration.

20. Composition according to any of the preceding claims, characterized in that it is provided as tablet, effervescent tablet, sachet, aromatized effervescent sachet, tab, hydrogel, ophthalmic ointment, ophthalmic hydrogel or retal suppository.

21. Composition according to any of the preceding claims, characterized in that it is provided as controlled release tablet for oral application.

22. Composition according to claim 20 or 21, characterized in that it is provided as multi-layer tablet, especially a two-layer tablet, wherein
   one of the layers comprises meloxicam together with at least one pharmaceutically acceptable additive for rapid release and another layer comprises meloxicam optionally with a usual controlled release agent.

FIG. 1: Heat flow curves of free meloxicam (a) the physical mixture of meloxicam with β-cyclodextrin hydrate (B) and of the composition according to example IV/1 (C).

FIG. 2: Heat flow curves of free meloxicam (a) the physical mixture of melodicam with β-cyclodextrin hydrate (B) and of the composition according to example IV/2 (C).

Figure 3:
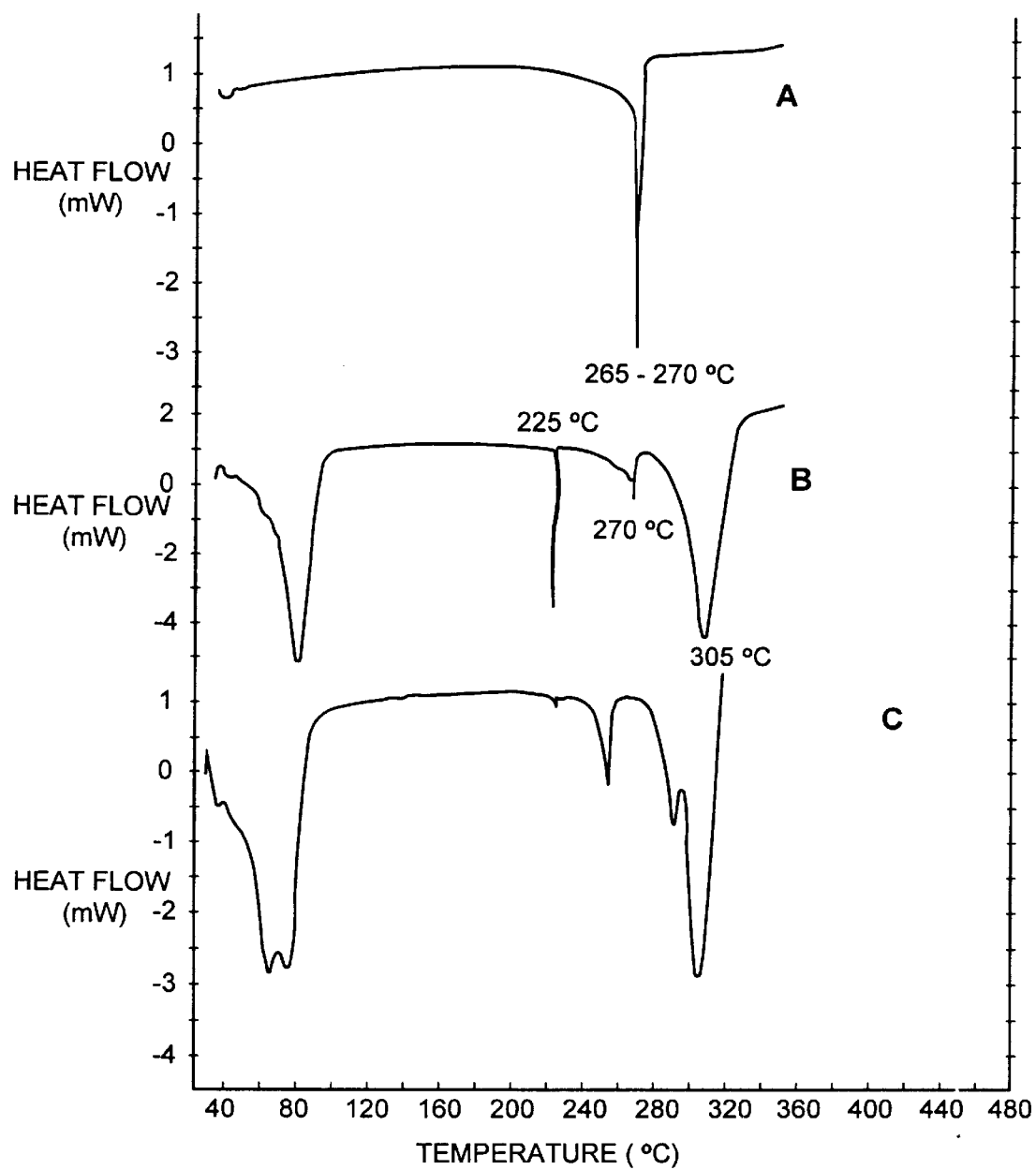

FIG. 3: Heat flow curves of free meloxicam (A) the physical mixture of meloxicam with β-cyclodextrin hydrate (B) and of the composition according to example IV/3 (C).

Figure 4:
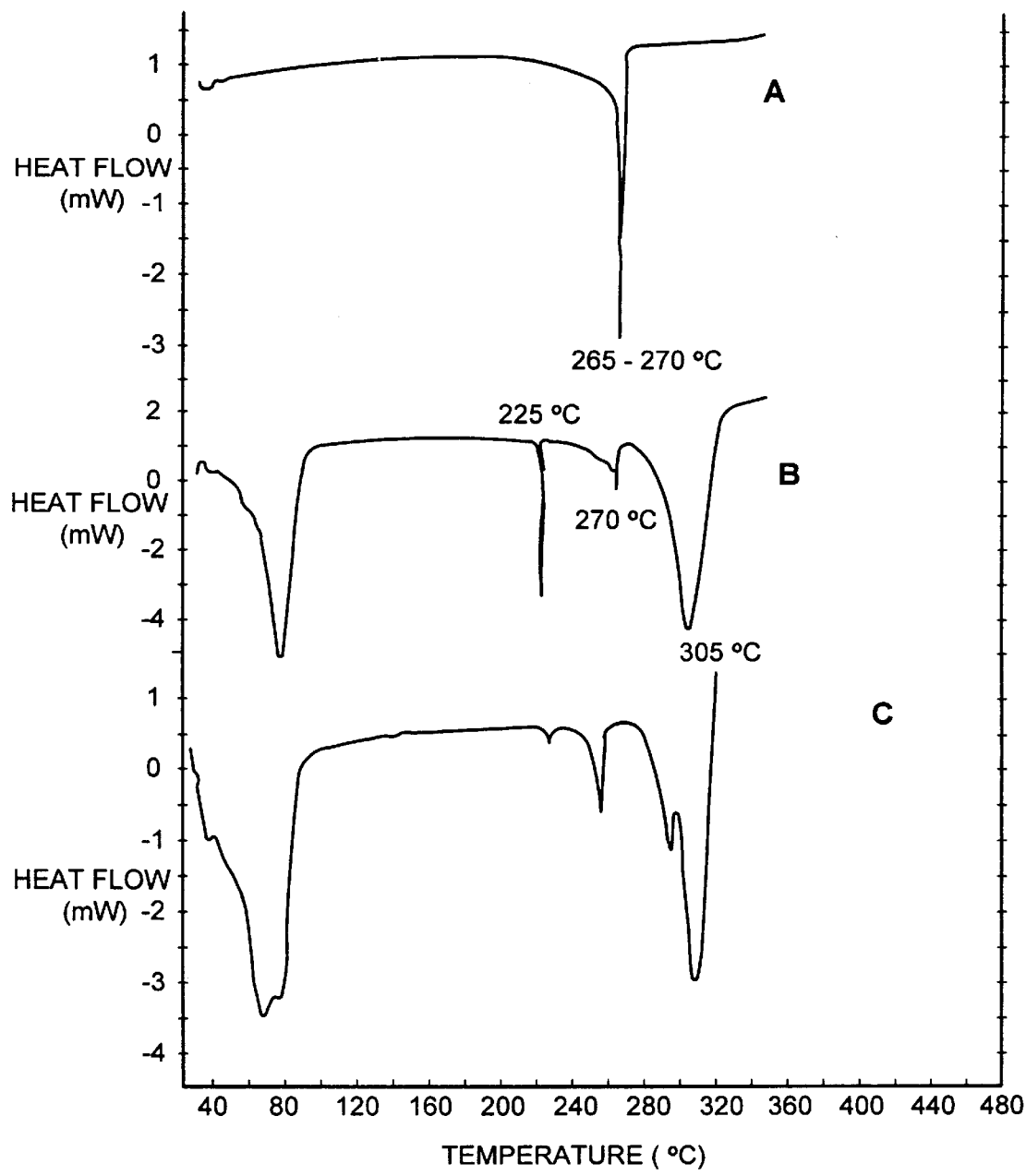

FIG. 4: Heat flow curves of free meloxicam (A) the physical mixture of meloxicam with β-cyclodextrin hydrate (B) and of the composition according to example IV/4 (C).

In order to describe the invention more specifically but without intending to limit the scope of the invention in any way the following examples are presented:

EXAMPLE I/1

10 g meloxicam and 90 g microcrystalline cellulose (AVICEL) were intensively co-ground for 6 hours at room temperature in a ceramic ball mill in presence of 0.25% (w/w) of the following surfactants:

TWEEN-80 and Solutol HS 15. The co-ground system was then dried to constant weight and passed through a 0.075 mm sieve.

The in vitro dissolution test shows that the composition according to example I/1 have significantly enhanced dissolution (table 1). The control composition consists of cellulose and meloxicam and was prepared under identical conditions as the surfactant-meloxicam-cellulose compositions.

TABLE 1

In vitro dissolution of meloxicam (at pH 7.6, 37° C.) from solid cellulose-based compositions after a 6-hour mechanical treatment.

| | dissolved meloxicam (in µg/ml) | | | |
|---|---|---|---|---|
| sample | 5. min. | 15. min | 30. min. | 45. min. |
| control | 115 | 225 | 280 | 478 |
| Tween-80 | 130 | 255 | 324 | 550 |
| Solutol | 145 | 280 | 400 | 590 |

Similar effects of the mentioned additives to the dissolution rates of meloxicam were observed at pH 6.6 in distilled water and at pH 1.2 in hydrochloric acid.

EXAMPLE II/1

25 g meloxicam were thoroughly milled in a ceramic ball mill at 25° C. for 6 hours with 75 g microcrystalline cellulose in presence of 5% (v/w) propylene glycol, polyethyleneglycol-400 (PEG-400) and glycerol, respectively. The composition was dried at 45° C. for constant weight yielding 102 g of slightly yellow solid with a meloxicam content of 24.6%. Dissolution-rates were determined in aqueous solution with pH 7.6 at 37° C. The improvement of the dissolution rate of meloxicam due to the mechanical treatment is shown in table 2. (Control composition was prepared under identical mechanical treatment of 25 g meloxicam and 75 g microcrystalline cellulose without co-solvents).

TABLE 2

Effect of co-solvents on the meloxicam dissolution in pH 7.6 buffer at 37° C.

| | dissolved meloxicam in µg/ml | | | |
|---|---|---|---|---|
| cosolvent | 5. min. | 15. min. | 30. min. | 45. min. |
| control | 120* | 231 | 379 | 490 |
| PEG 400 | 305 | 355 | 480 | 580 |
| prop. glycol | 290 | 360 | 460 | 550 |

EXAMPLE III/1

25 g meloxicam and 75 g lactose were intensively co-ground in a ball mill for 4 hours without (control) and in presence of 20% (by weight) of nicotinamide and 20% of sodium-glycinate, respectively. The solid compositions were sieved through a 0.071 mm sieve and tested for meloxicam dissolution at pH=1.2 at 37° C. Results are listed in table 3.

TABLE 3

Effect of hydrotropic additives to the meloxicam dissolution rate in pH 1.2 buffer at 37° C.

| | dissolved meloxicam in pg/ml | | | |
|---|---|---|---|---|
| hydrotropes | 5. min. | 15. min. | 30. min. | 45. min. |
| control | 0.20* | 0.70 | 0.76 | 0.75 |
| Na-glycinate | 0.60 | 0.75 | 0.80 | 0.80 |
| nicotinamide | 0.80 | 0.85 | 0.98 | 0.90 |

EXAMPLE IV/1

The co-grinding of the solid components meloxicam and beta-cyclodextrin hydrate (BCDX) in a ceramic ball-mill for sufficient time results at ambient temperature in novel type solid state-structure of these solids, as proved by X-ray diffractometry and also by microscopy. The composition after grinding process also exhibited an improved dissolution profile compared to meloxicam, ground alone under the same conditions.

Thus 11.35 g crystalline beta-cyclodextrin hydrate (BCDx) with 13.8% water content and 1.76 g crystalline meloxicam were intensively ball-milled for 6 hours at 25° C. to reach metastable amorphous state. The resulting solid composition was passed through a sieve of 250 µm.

Characteristics of the meloxicam composition according to example IV./1.: The product appears as a slightly yellow, free-flowing, non-hygroscopic powder.

As high resolution Differential Scanning Calorimetry investigations indicate this composition shows two distinct endothermic peaks—related to meloxicam—on the heat-flow curve at 255° C., 280° C. This phenomenon is attributed most probably to the co-existence of different solid state prototropic forms of the drug which are generated by the mechanical manipulation in presence of the hydrated beta-cyclodextrin. The DSC of pure meloxicam shows a melting endothermic heat flow at 267–270° C. which is in good agreement with literature data of the melting point of meloxicam (268° C.). (See FIG. 1.)

The meloxicam content of the composition according to example IV/1. is 13.1% and the product has a loss of weight between 5.9–6.6% after the drying. The X-ray powder diffraction analysis of the ball milled co-ground system according to example IV/1. indicates that the micronisation treatment results in the decrease of crystallinity, but without complete amorphisation of the system.

The solution characteristics of the meloxicam composition according to example IV/1. is shown in table 4.

The following standard method was used for the determination of the solution rate of the drug compositions: In vitro dissolution properties of the cyclodextrin based meloxicam compositions were studied under non-sink conditions in two different buffer systems, pH 1.3 and 7.6, respectively and in deionised water (pH=6.6) at 37° C.

The stirring rate was 160 r.p.m. To ensure comparable particle size distribution the samples were passed through a sieve of 80 mesh prior to dissolution testing. Sampling time intervals were 5, 10, 15, 30, 45 and 60 minutes.

TABLE 4

In vitro rates of dissolution of free meloxicam and of the composition according to example IV./1. at pH 1.3 and 7.6 at 37° C.
Dissolved meloxicam in solution in µg/ml

| minutes | free meloxicam | | composition according to example IV/1. | |
| --- | --- | --- | --- | --- |
| | pH: 1.3 | pH: 7.6 | pH: 1.3 | pH: 7.6 |
| 5 | 0.30 | 38 | 2.5 | 975 |
| 10 | 0.38 | 218 | 2.6 | 981 |
| 15 | 0.44 | 320 | 2.7 | 1026 |
| 30 | 0.56 | 390 | 2.8 | 1046 |
| 45 | 0.59 | 485 | 2.7 | 1091 |
| 60 | 0.65 | 550 | 3.9 | 1117 |

The solubility enhancement at gastric pH was about 5-fold.

EXAMPLE: IV/2

1.0 g meloxicam, 9.0 g beta-CD hydrate (BCDx), 0.01 g Methocel® and 5 ml of deionised water were added to a ceramic mortar and were intensively co-kneaded for 45 minutes at room temperature. The wet homogenisate was passed through a 2 mm sieve and dried at 40° C. yielding a hard, yellowish solid. The dry product was sieved through a 0.25 mm sieve. (9.53 g, meloxicam content: 8.7% by weight.)

The solid state investigation of the product according to example IV/2. by DSC revealed the existence of a novel type of structure of the active ingredient, which is characterized by DSC heat-flow curves at the temperature range of 160–320° C. This indicates the co-existence of two different allotropic forms of meloxicam, evidenced by negative enthalpy changes (melting) at around 250 and 293° C. respectively. None of these enthalpy changes are identical with the sharp melting heat flow of meloxicam itself that appears at 264–266° C. The simple mechanical mixture of meloxicam with beta-CD hydrate resulted in a composition that had a DSC pattern with a melting range (255–265° C.) near the melting point of meloxicam. (See FIG. 2.)

Dissolution characteristics of the product according to example IV/2. are shown in table 5.

TABLE 5

In vitro rates of dissolution of free meloxicam (130 mg) and of the composition according to example IV./2. (1500 mg) at pH 1.3 and 7.6, 37° C.
Dissolved meloxicam in solution in µg/ml

| minutes | free meloxicam | | composition according to example IV/2. | |
| --- | --- | --- | --- | --- |
| | pH: 1.3 | pH: 7.6 | pH: 1.3 | pH: 7.6 |
| 5 | 0.45 | 38 | 7.4 | 917 |
| 10 | 0.62 | 218 | 7.8 | 990 |
| 15 | 0.67 | 320 | 7.7 | 1067 |
| 30 | 0.74 | 390 | 7.7 | 1077 |
| 45 | 0.73 | 485 | 7.9 | 1149 |
| 60 | 0.67 | 550 | 6.4 | 1199 |

EXAMPLE: IV/3

1.0 meloxicam, 9.0 g of beta-CD hydrate (BCDx), 0.01 g of tris-hydroxymethyl-aminomethane and 5 ml of deionised water were added to a twin-screw kneader and were intensively co-kneaded for 45 minutes at room temperature. The wet homogenisate was passed through a 2 mm sieve and dried at 40° C. yielding a hard, yellowish extrudate. The dry, solid product was sieved through a 0.25 mm sieve. (Yield: 10.03 g yellow powder, meloxicam content: 8.9% by weight.)

The DSC pattern of the product according to example IV./3. showed the co-existence of two different allotropic forms of meloxicam with the characteristic negative enthalpy changes of 256 and 294° C. (See FIG. 3.)

Dissolution characteristics of the product according to Example IV/3. in comparison with free meloxicam are shown in table 6.

TABLE 6

In vitro rates of dissolution of free meloxicam (130 mg) and of the composition according to example IV./3. (1500 mg) at pH 1.3 and 7.6 at 37° C.
Dissolved meloxicam in solution in µg/ml

| minutes | free meloxicam | | composition according to example IV/3. | |
| --- | --- | --- | --- | --- |
| | pH: 1.3 | pH: 7.6 | pH: 1.3 | pH: 7.6 |
| 5 | 0.45 | 38 | 6.8 | 1237 |
| 10 | 0.62 | 218 | 6.1 | 1252 |
| 15 | 0.67 | 320 | 5.9 | 1278 |
| 30 | 0.74 | 390 | 6.7 | 1280 |
| 45 | 0.73 | 485 | 6.1 | 1287 |
| 60 | 0.67 | 550 | 5.2 | 1310 |

EXAMPLE: IV/4

1.0 meloxicam, 9.0 g of beta-CD hydrate (BCDx), 0.01 g of 2.6 -diamino-haxanoic acid (DL-lysine) and 5 ml of deionised water were added to a twin-screw kneader and were intensively co-kneaded for 45 minutes at room temperature. The wet mixture was dried at 40° C. yielding a hard, yellowish solid. The dry, solid product was sieved through a 0.25 mm sieve. (Yield: 9.9 g yellow powder, with a meloxicam content of 9.8% by weight.)

Thermoanalytical study proved the existence of two different types of solid forms of meloxicam with melting heat flow curves at around 256 and 292° C. respectively.(See FIG. 4.)

The improvement of dissolution characteristics of the product according to example IV/4. in comparison with free meloxicam are shown table 7.

TABLE 7

In vitro rates of dissolution of free meloxicam (130 mg)
and of the composition according to example IV./4. (1300 mg)
at pH 1.3 and 7.6 at 37° C.
Dissolved meloxicam in solution in µg/ml

| minutes | free meloxicam | | composition according to example IV/4. | |
|---|---|---|---|---|
| | pH: 1.3 | pH: 7.6 | pH: 1.3 | pH: 7.6 |
| 5 | 0.45 | 38 | 6.9 | 1134 |
| 10 | 0.62 | 218 | 4.8 | 1150 |
| 15 | 0.67 | 320 | 4.9 | 1160 |
| 30 | 0.74 | 390 | 4.9 | 1175 |
| 45 | 0.73 | 485 | 4.3 | 1187 |
| 60 | 0.67 | 550 | 4.6 | 1217 |

EXAMPLE: IV/5

15.2 g 6-mono-amino-beta-cyclodextrin (AMBCDx), 3 ml water and 1.8 g crystalline meloxicam were intensively kneaded for 60 minutes at 25° C. The resulting wet mixture was passed through a 2 mm sieve and dried at 40° C. to constant weight. The resulting yellowish solid was milled into a fine powder and sieved through a 0.25 mm sieve. Yield: 16.6 g powder with a meloxicam content of 10.4% by weight.

The solid meloxicam composition according to example IV/5. showed significantly improved dissolution.

The improved dissolution of meloxicam composition according to example IV/5. is shown in table 9.

TABLE 9

The in vitro rate of dissolution of meloxicam composition according to example IV/5. (pH: 1.2, at 37° C.)

| minutes | meloxicam (µg/ml) |
|---|---|
| 5 | 7.7 |
| 10 | 9.0 |
| 30 | 9.2 |
| 45 | 9.5 |
| 60 | 9.5* |

*control: meloxicam showed a dissolution rate of 0.8 µg/ml at 60 min.

EXAMPLE IV/6

113. 5 g solid, dry beta cyclodextrin hydrate (BCDX) are mixed thoroughly with 35.14 g crystalline meloxicam at 25° C. in a high-speed twin-screw kneader for 10 minutes. 7.43 g polyethyleneglycol (PEG-400) are added to the kneading machine. The reaction mixture is thoroughly kneaded for 0.5 hours at 60° C., then for 2 hours at 25° C. The resulting composition is directly transferred into a granulating machine and the granulation process is performed in the presence of 10 ml of a 0.1% aqueous sodium-corboxymethyl-cellulose solution. The granules are dried at 40° C. to constant weight.

The resulting free-flowing, slightly yellow granules can be used directly for tabletting.

Yield: 155 g granule, with a meloxicam content of 22.0%.

EXAMPLE IV/7

129.7 g crystalline gamma-cyclodextrin (GCDX) hydrate are intensively co-milled at room temperature in a ceramic ball mill with 17.57 g solid meloxicam for 3 hours at 25° C. Yield: 146.2 g of slightly yellow, powder is obtained. The solid composition appears as a nearly amorphous powder with a meloxicam content of 11.8% by weight and exhibits an enhanced dissolution in water.

EXAMPLE IV/8

16 g branched-beta-cyclodextrin (a glucosyl-maltosyl-substituted type, enzyme-modified beta-CDx derivative) are intensively kneaded in a twin-screw kneader with 1.8 g meloxicam in presence of 2.0 ml propyleneglycol for 30 minutes at 40° C. until a dense creamy paste is obtained. The paste is kneaded further for additional 3 hours at 25° C., and dried at room temperature to constant weight. The dry product appears as a slightly yellow-coloured, hard solid which is further ground to give a fine powder and passed through a 250 µm sieve. Yield: 17.5 g yellow, slightly hygroscopic, amorphous powder, with a meloxicam content of 10.0%. The loss of weight by drying of the sample according to example 8. is 6.0%.

EXAMPLE IV/9

16 g hydroxypropyl-beta-cyclodextrin (with a degree of hydroxyalkylation between 4.0–5.0 ) are intensively mixed in powder form in a ceramic ball mill with 1.8 g of meloxicam. The mixture is then further co-milled for 3 hours at 25° C. to reach desired metastable physical state. Yield: 17.2 g yellowish, amorphous powder, meloxicam content:10.0%. The drying loss of the product according to example IV/9. is 4.3% and the sample appears to be amorphous by powder X-ray diffraction.

EXAMPLE IV/10

4.54 g beta cyclodextrin hydrate (BCDX) are wetted with 1 ml water and kneaded in a ceramic mortar with 0.702 g crystalline meloxicam at 25° C. for 15 minutes. Then 0.24 g solid nicotinamide are added to the mixture and the three-component solid system is further kneaded for 30 minutes at 25° C. The mixture is dried at 45° C. to constant weight. Yield: 5.1 g of slightly yellow powder, with a meloxicam content of 11.9% by weight. The composition according to example IV/10. shows significantly improved dissolution rates in a pH 7.6 buffer at 25° C. compared to meloxicam.
(See table 11.)

TABLE 11

In vitro rates of dissolution of free meloxicam and
of the composition according to example IV/10. at pH 1.3 and 7.6
at 37° C.
Dissolved meloxicam in solution in µg/ml

| minutes | free meloxicam | | composition according to example IV/10. | |
|---|---|---|---|---|
| | pH: 1.3 | pH: 7.6 | pH: 1.3 | pH: 7.6 |
| 5 | 0.4 | 38 | 7.2 | 880 |
| 10 | 0.6 | 188 | 10 | 900 |
| 15 | 0.7 | 320 | 12 | 1100 |
| 30 | 0.7 | 390 | 12 | 1246 |
| 45 | 0.7 | 485 | 14.7 | 1391 |
| 60 | 0.6 | 550 | 13.9 | 1388 |

EXAMPLE IV/11

10.5 g beta-cyclodextrin-hydrate were mechanically treated by intense co-grinding with 1.6 g solid meloxicam and 1.5 g diethanolamine for 30 minutes at 40° C., and for 2 hours at 25° C. The resulting slightly yellow mixture was dried at 45° C. to constant weight and passed through a 0.071 mm sieve. The obtained solid composition had a meloxicam content of 11.9% by weight.

The dissolution rate of the composition according to example IV/12. is shown in table 13.

TABLE 13

In vitro dissolution of free meloxicam and of the composition according to example IV/12. at pH 1.3 and in deionised water (pH = 6.6) at 37° C.
Dissolved meloxicam in solution in µg/ml

|  | free meloxicam | | Composition according to example IV/12. | |
| --- | --- | --- | --- | --- |
| minutes | pH: 1.3 | pH: 6.6 | pH: 1.3 | pH: 6.6 |
| 5 | 0.4 | 23 | 8.0 | 700 |
| 10 | 0.6 | 148 | 8.3 | 626 |
| 15 | 0.7 | 232 | 9.6 | 659 |
| 30 | 0.7 | 390 | 10.1 | 780 |
| 45 | 0.7 | 415 | 10.0 | 896 |
| 60 | 0.6 | 475 | 12.1 | 940 |

The use of other pharmaceutically acceptable amines with a high bioling point (like ethylenediamine, monoethanolamine, triethanolamine, di-isopropylamine, dibutylamine, pentylamine etc.) and of other pharmaceutically acceptable solid alkalizing agents (like sodium-carbonate, ammonium-carbonate, powdered sodium-hydroxide, sodium-phosphate, etc.)resulted in improved solubility and bioavailability.

EXAMPLE IV/12

113.5 g solid, beta cyclodextrin hydrate (BCDx) are intensively co-milled in a ceramic ball mill with high energy with 35.14 g crystalline meloxicam and 0.5 g sodium carbonate at 25° C. for 30 minutes.

Yield: 147.6 g slightly yellow, free-flowing powder with a meloxicam content of 22.0%. The solid composition appears to be almost amorphous by powder X-ray diffraction.

EXAMPLE V/1

Formulation of aromatised sachets equivalent to 7,5 mg meloxicam as active ingredient.

| Meloxicam composition according to example IV/1. | 58 mg |
| --- | --- |
| Sucrose | 788 mg |
| Orange flavour granulate | 14,5 mg |
| Ascorbic acid | 7,25 mg |
| Methylglucamin | 2,0 mg |

EXAMPLE V/2

Preparation of an immediate releasing tablet containing 7,5 mg meloxicam per tablet.

| Meloxicam composition according to example IV/1 | 58 mg |
| --- | --- |
| Lactose 1 H₂O | 531 mg |
| Maize starch | 251 mg |
| PVP XL | 100 mg |
| Aerosil 200 | 50 mg |
| Magnesium Stearate | 10 mg |

EXAMPLE V/3

A 10 mg/g meloxicam hydrogel formulation is prepared as follows:

| Micronised meloxicam composition according to example IV/9., equivalent to 10 mg of meloxicam | 100,0 mg |
| --- | --- |
| Hydroxypropylmethylcellulose | 215,0 mg |
| Propylenglycol | 2500,0 mg |
| PEG-7-glyceryl-coconat | 300,0 mg |
| Isopropylalcohol | 500,0 mg |
| Deionised water | 6385,0 mg |

EXAMPLE V/4

Ophthalmic Ointment:

In a Diosna cream-homogeniser a previously sterilized meloxicam composition according to example IV/12. is thoroughly mixed for 60 minutes with ophthalmic cream base at 25° C. having the following ingredients:

| Aqua destillata | 29.0 g |
| --- | --- |
| Cera flava | 16.0 g |
| Paraffin subliquidum | 48.0 g |
| Calcium stearinicum | 4.5 g |
| Meloxicam composition according to example IV/13 | 2.5 g |

EXAMPLE V/5

Preparation of an Ophthalmic Hydrogel.

The ophthalmic hydrogel formulation is prepared by dispersing meloxicam-composition according to example IV/4.

| Water with 0.002% thiomersal | 95 g |
| --- | --- |
| Carbopol ® 940 | 0.9 g |
| Diisopropanolamine | 1.0 g |
| Meloxicam-composition according to example IV/4. | 3.1 g |

EXAMPLE V/6

Preparation of a Rectal Suppository.

The rectal suppository is prepared by mixing meloxicam-composition according to example IV/7. at 40° C. with a previously molten hydrophilic suppository base consisting of Massa polyoxaetheni base. The composition of suppositories is 15 mg of meloxicam per suppository. Thus 127 mg of meloxicam- composition according to example IV/7. is mixed with 1873 mg of Massa polyoxaetheni base resulting in a 2 g suppository.

EXAMPLE V/7

Preparation of a Two-layered Tablet

In a first step the tabletting mass for the initial dose is prepared. The components of the initial dose are:

| | |
|---|---|
| Meloxicam-cyclodextrin (equivalent to 2,5 mg meloxicam) | 19,1 mg |
| Lactose 1 H$_2$O | 11,5 mg |
| Calcium hydrogen phosphate 2 H$_2$O | 15,3 mg |
| Microcristalline cellulose | 18,7 mg |
| Maize starch | 7,6 mg |
| Sodium starch glycollate | 3,0 mg |
| Colloidal anhydrous silica | 0,4 mg |
| Magnesium stearate | 0,8 mg |
| Red ferric oxide | 0,04 mg |

They are sieved through a 0,8 mm sieve and homogenised in a container mixer for 20 min./5 rpm.

In a second step the granules for the controlled release layer are prepared. Meloxicam (5 mg), lactose 1 H$_2$O (56,3 mg), methyl-hydroxypropylcellulose (12,5 mg), Crospovidone (2 mg) are granulated with purified water in a fluid bed granulator Magnesium stearate(0,375 mg), colloidal anhydrous silica (0,25 mg) and sodium lauryl sulphate (0,125 mg) are added. The mixture is sieved through a 1,0 mm sieve and mixed in a container mixer for 20 min/ 5 rpm.

The slow release granules of above are compressed in a first run and the granules of the initial dose are added onto the controlled release layer and compressed as a second layer.

EXAMPLE V/8

Preparation of an Effervescent Tablet Containing 7,5 mg Meloxicam per Tablet.

| | |
|---|---|
| Meloxicam composition according to example IV/1 | 58 mg |
| Methylglucamin | 2 mg |
| Sodium hydrogen carbonate | 260 mg |
| Sodium hydrogen tartrate | 320 mg |
| Aspartame | 35 mg |
| Flavoring substances | 77 mg |

EXAMPLE V/9

Preparation of an Effervescent Tablet Containing 7,5 mg Meloxicam per Tablet (3,142 g).

| | |
|---|---|
| Meloxicam composition according to example IV/1 | 58 mg |
| Lactose 1 H$_2$O | 1102 mg |
| Docusate Sodium | 5,8 mg |
| Polydimethylsiloxane | 16,24 mg |
| Polyvinylpyrrolidone | 37,7 mg |
| Citric acid | 942,5 mg |
| Sodium hydrogen carbonate | 333,5 mg |
| Sodium sulfate | 348 mg |
| Saccharin Sodium | 8,7 mg |
| Aspartame | 58 mg |
| Flavoring agents | 87 mg |

EXAMPLE V/10

Preparation of a Tablet Containing 7,5 mg Meloxicam per Tablet.

| | |
|---|---|
| Meloxicam composition according to example IV/1 | 58 mg |
| Lactose 1 H$_2$O | 490,1 mg |
| Microcrystalline Cellulose | 145 mg |
| Crospovidone | 23,2 mg |
| Magnesium Stearate | 4,35 mg |
| Colloidal Anhydrous Silica | 2,5 mg |
| Sodium Lauryl Sulfate | 1,45 mg |

The disclosure comprises also that of the attached application EP 97 114 816.8.

What is claimed is:

1. Pharmaceutical composition comprising meloxicam as active ingredient, a cyclodextrin, a facultative oligosaccharide other than cyclodextrin, a facultative polysaccharide, one or more pharmaceutically acceptable additives selected from the group consisting of surfactants, hydrotropic agents, alkalizing agents, hydrocolloids and polymers and facultative excipients, carriers and/or auxiliary agents, wherein the pharmaceutical composition is obtainable by co-milling, co-grinding or co-kneading meloxicam in the presence of cyclodextrin as a pharmaceutically acceptable additive.

2. Composition according to claim 1, obtainable by micronizing meloxicam in the presence of cyclodextrin as a pharmaceutically acceptable additive.

3. Composition according to claim 1, obtainable by wet mechanical homogenization of its components in the presence of water, preferably in an amount of 5 to 50% by weight (based on the total weight of the composition).

4. Composition according to claim 1, characterized by microcrystalline cellulose and/or lactose and/or starch as oligo- or polysaccharide.

5. Composition according to claim 1, characterized by polyoxyethylene-sorbitan-mono-fatty acid, diethyleneglycol monoethylether and/or nonylphenol tetraethyleneglycol ether as surfactant.

6. Composition according to claim 1, characterized by an amount of 1 to 99 and preferably about 20% by weight of a hydrotropic agent (based on the total weight of the composition).

7. Composition according to claim 1, characterized by sodium glycinate, nicotinamide and/or methylglucamine as hydrotropic agent.

8. Composition according to claim 1, characterized by sodium carbonate, ammonium carbonate, sodium hydroxide, especially powdered sodium hydroxide, and/or sodium phosphate as alkalizing agent.

9. Composition according to claim 1, characterized by β-cyclodextrin hydrate (BCDx), 6-monoamino-beta-cyclodextrin (AMBCDx), gamma-cyclodextrin hydrate (GCDX), branched β-cyclodextrin, especially a branched β-cyclodextrin of the glycosyl/maltosyl substituted type or a β-cyclodextrin hydrate derivative, and/or hydroxypropyl-β-cyclodextrin as cyclodextrin, especially of a hydroxyalkylation degree in the range of 4.0 to 5.0.

10. Composition according to claim 1, characterized by methylcellulose-propylene-glycol ether, tris-hydroxymethylaminomethane, 2,6-diamino-hexanoic acid (D,L-lysine), mannitol, polyethyleneglycol, propyleneglycol, diethanolamine, ethyleneamine, monoethanolamine, triethanolamine, diisopropylamine, dibutylamine, pentylamine, sodium dodecylsulfate, methylglucamine, polyvinylpyrrolidone, cellulose ether, polyoxyethylene-polyoxypropylene-block-copolymers and/ or nicotinamide as pharmaceutically acceptable additive.

11. Pharmaceutical composition comprising meloxicam as active ingredient, a cyclodextrin and a facultativen oligosaccharide or polysaccharide, water as aqueous vehicle, a co-solvent and facultative auxiliary agents, wherein the pharmaceutical composition is obtainable by micronizing meloxicam in the presence of the cyclodextrin, the facultative oligosaccharide or polysaccharide, water and a co-solvent as pharmaceutically acceptable additive.

12. Pharmaceutical composition comprising meloxicam as active ingredient, a cyclodextrin and a facultative oligosaccharide or polysaccharide, water as aqueous vehicle, a co-solvent and facultative auxiliary agents, obtainable by wet mechanical homogenization of its components in the presence of water, preferably in an amount of 5 to 50% by weight (based on the total weight of the composition).

13. Composition according to claim 11, characterized by β-cyclodextrin hydrate (BCDx), 6-monoamino-beta-cyclodextrin (AMBCDx), gamma-cyclodextrin hydrate (GCDx), branched β-cyclodextrin, especially a branched β-cyclodextrin of the glycosyl/maltosyl substituted type or a β-cyclodextrin hydrate derivative, and/or hydroxypropyl-β-cyclodextrin as cyclodextrin, especially of a hydroxyalkylation degree in the range of 4.0 to 5.0.

14. Composition according to claim 11, characterized by microcrystalline cellulose, lactose and/or starch as oligo- or polysaccharide.

15. Composition according to claim 11, characterized by an amount of 0.1 to 25 and preferably about 5.0% by weight co-solvent (based on the amount of water or on the total weight of the composition).

16. Composition according to claim 11, characterized by i-propanol, propyleneglycol, glycerol, polyethyleneglycol and/or ethanol as co-solvent.

17. Composition according to claim 11, characterized by one ore more additional pharmaceutical acceptable additives selected from the group consisting of surfactants, hydrotrbpic agents, alkalizing agents, hydrocolloids and polymers, preferably selected from the group consisting of methylcellulose-propylene-glycol ether, tris-hydroxymethylaminomethane, 2,6-diamino-hexanoic acid (D,L-lysine), mannitol, polyethyleneglycol, propyleneglycol, diethanolamine, ethyleneamine, monoethanolamine, triethanolamine, diisopropylamine, dibutylamine, pentylamine, sodium carbonate, sodium dodecylsulfate, ammonium carbonate, sodium hydroxide, especially powdered sodium hydroxide, sodium phosphate, methylglucamine, polyvinylpyrrolidone, cellulose ether, polyoxyethylene-polyoxypropylene-block-copolymers and/ or nicotinamide as pharmaceutically acceptable additive.

18. Composition according to claim 11, characterized by an amount of 1 to 99 and preferably about 20% by weight of a hydrotropic agent (based on the total weight of the composition).

19. Composition according to claim 1 for oral, rectal, transdermal, ophthalmic or parenteral administration.

20. Composition according to claim 1, characterized in that it is provided as tablet, effervescent tablet, sachet, aromatized effervescent sachet, tab, hydrogel, ophthalmic ointment, ophthalmic hydrogel or retal suppository.

21. Composition according to claim 1, characterized in that it is provided as controlled release tablet for oral application.

22. Composition according to claim 20, characterized in that it is provided as multi-layer tablet, especially a two-layer tablet, wherein one of the layers comprises meloxicam together with at least one pharmaceutically acceptable additive for rapid release and another layer comprises meloxicam optionally with a usual controlled release agent.

* * * * *